(12) United States Patent
Goris et al.

(10) Patent No.: US 11,375,960 B2
(45) Date of Patent: Jul. 5, 2022

(54) DETECTION AND COMPENSATION METHOD FOR MONITORING THE PLACE OF ACTIVITY ON THE BODY

(71) Applicant: Koninklijke Philips N.V., Eindhoven (NL)

(72) Inventors: Annelies Goris, Eindhoven (NL); Maarten Peter Bodlaender, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 248 days.

(21) Appl. No.: 16/518,390

(22) Filed: Jul. 22, 2019

(65) Prior Publication Data

US 2019/0343464 A1 Nov. 14, 2019

Related U.S. Application Data

(63) Continuation of application No. 15/064,869, filed on Mar. 9, 2016, now Pat. No. 10,398,388, which is a
(Continued)

(30) Foreign Application Priority Data

Dec. 15, 2005 (EP) ..................................... 05112250

(51) Int. Cl.
*A61B 5/00* (2006.01)
*A61B 5/06* (2006.01)
*A61B 5/11* (2006.01)

(52) U.S. Cl.
CPC ............ *A61B 5/7267* (2013.01); *A61B 5/061* (2013.01); *A61B 5/065* (2013.01); *A61B 5/1118* (2013.01);
(Continued)

(58) Field of Classification Search
CPC ... A61B 5/7267; A61B 5/7253; A61B 5/7275; A61B 5/061; A61B 5/065; A61B 5/1118;
(Continued)

(56) References Cited

U.S. PATENT DOCUMENTS 5,111,826 A 5/1992 Nasiff
5,573,013 A 11/1996 Conlan
(Continued)

FOREIGN PATENT DOCUMENTS

EP 1254629 A1 11/2002
EP 1915590 A4 4/2008
(Continued)

OTHER PUBLICATIONS

Plasqui, G., "Daily Physical Activity, Energy Expenditure and Physical Fitness: Assessment and Implications", Doctoral Thesis, Maastricht University, 2004, 134 page document.

*Primary Examiner* — Sean P Dougherty

(57) ABSTRACT

A measuring system (1) comprises a sensor (6) arranged to be attached to a subject for obtaining a measured value representing a physical or a physiological quantity of the subject. The measuring system further comprises means for deriving a subject-related value from the measured value. The sensor is arranged to be attached at one of a plurality of positions on the subject. The measuring system further comprises means for establishing the position of the sensor on the subject. The means for deriving the subject-related value is arranged for deriving the subject-related value also in dependence on the position of the sensor on the subject.

20 Claims, 5 Drawing Sheets

Related U.S. Application Data continuation of application No. 12/097,121, filed as application No. PCT/IB2006/054599 on Dec. 5, 2006, now Pat. No. 9,314,192.

(52) U.S. Cl.
CPC ............ *A61B 5/681* (2013.01); *A61B 5/7253* (2013.01); *A61B 5/7275* (2013.01); *A61B 2560/0223* (2013.01); *A61B 2562/0219* (2013.01)

(58) Field of Classification Search
CPC ............ A61B 5/681; A61B 2560/0223; A61B 2562/0219
See application file for complete search history.

(56) References Cited

U.S. PATENT DOCUMENTS

| | | | |
|---|---|---|---|
| 6,127,672 A | 10/2000 | Danisch | G01B 11/18 |
| | | | 250/227.14 |
| 6,893,407 B1 | 5/2005 | Brooks | G06F 3/016 |
| | | | 600/300 |
| 6,941,239 B2 | 9/2005 | Unuma et al. | |
| 2001/0049470 A1 | 12/2001 | Mault et al. | |
| 2002/0109600 A1 | 8/2002 | Mault et al. | |
| 2003/0065257 A1 | 4/2003 | Mault et al. | |
| 2003/0226695 A1 | 12/2003 | Mault | |
| 2004/0034289 A1 | 2/2004 | Teller et al. | |
| 2004/0077975 A1 | 4/2004 | Zimmerman | A61B 5/1116 |
| | | | 600/595 |
| 2004/0102931 A1 | 5/2004 | Ellis et al. | |
| 2005/0010139 A1 | 1/2005 | Aminian | A61B 5/1038 |
| | | | 600/595 |
| 2006/0161079 A1 | 7/2006 | Choi | A61B 5/1117 |
| | | | 600/595 |
| 2007/0032981 A1 | 2/2007 | Merkel et al. | |
| 2007/0167846 A1 | 7/2007 | Sternickel | A61B 5/04007 |
| | | | 600/509 |

FOREIGN PATENT DOCUMENTS

| | | |
|---|---|---|
| JP | 2003102692 A | 4/2003 |
| JP | 2005230340 A | 9/2005 |
| KR | 100601981 B1 | 7/2006 |
| WO | WO2005070289 A1 | 8/2005 |
| WO | 2007016584 A2 | 2/2007 |

DETECTION AND COMPENSATION METHOD FOR MONITORING THE PLACE OF ACTIVITY ON THE BODY

CROSS REFERENCE TO RELATED APPLICATIONS

The present application is a continuation of U.S. patent application Ser. No. 15/064,869, filed on Mar. 9, 2016, which is a continuation of U.S. patent application Ser. No. 12/097,121, filed on Jun. 12, 2008, which is the U.S. National Phase application under 35 U.S.C. § 371 of International Application No. PCT/IB2006/054599, filed on Dec. 5, 2006, which claims the benefit of European Patent Application No. 05112250.5, filed Dec. 15, 2005. These applications are hereby incorporated by reference herein.

FIELD OF THE INVENTION

The invention relates to a measuring system comprising
a sensor arranged to be attached to a subject for obtaining a measured value representing a physical or a physiological quantity of the subject, and
means for deriving a subject-related value from the measured value.
The invention also relates to a system for determining the calorie balance of a subject, and to a method of estimating a subject-related derived value.

BACKGROUND OF THE INVENTION

Overweight and obesity are growing problems; for example over 60% of the American population can be classified as overweight or obese. Weight gain occurs when a human has a higher energy intake (food) than energy expenditure (resting metabolic rate+activity). Since this unbalance causes the weight gain problem, many weight loss programs require that users log the food consumed and activities done in order to estimate the calorie balance.

Tables and equations exist for converting nutrition values and activities into calorie intake and expenditure, respectively. However, manual calorie counting is a cumbersome process requiring knowledge, time, effort, recording and discipline. Thus, calorie logging is a problem for many people and hence it is a challenge for researchers to find a solution therefore.

In US patent application publication US2003/0065257, a combination of a diet and activity-monitoring device is described for monitoring both the consumption and activity of the subject. Such a monitoring device includes a body activity monitor for monitoring the body activity of the subject. The body activity monitor is operable to output a signal indicative of the subject's body activity. An activity calculator may also be provided, which receives the activity indicative signal and determines body activity level and/or energy expenditure for the subject. The monitoring device may take the form of a wristwatch-style device or a belt or clothing-mounted monitor. The monitoring device may comprise a heart rate monitor. The heart rate of the subject increases with activity and decreases when the subject is resting. The activity monitor may be calibrated using an indirect calorimeter. The heart rate sensor may be part of the wristwatch-style activity monitor, or it may be provided as a separate unit, for example in the form of a chest-strap, which communicates with the activity monitor.

The activity monitor may alternatively comprise a motion sensor such as a mechanical pendulum or a single or multi-axis accelerometer. An accelerometer is preferred since it may provide information on body movement as well as the direction and intensity of the movement. The motion sensor may form part of the wristwatch or belt or clothing-mounted monitoring device or may be part of a separate accessory that communicates with the monitoring device. The body activity monitor may be calibrated to determine activity-related energy expenditure using an indirect calorimeter.

As another alternative, the body activity monitor may include multiple modes for recording a variety of activities, such as swimming, biking, and use of stationary exercise equipment. The subject presses a start button and the body activity monitor will record the duration of the activity.

Furthermore, the monitoring device also preferably includes a consumption notation control for use by the subject to indicate when the subject consumes food. The body activity monitor and the consumption notation control may take a variety of forms. It may include a GPS antenna to determine the position of the subject using GPS signals. It may combine a time-indicative signal with the GPS signals to determine changes in position of the subject as well as the rate of change in position. This allows determination of movement or body activity. The device may be calibrated to determine caloric expenditure from the measured body activity.

Moreover, a position and/or activity discriminator may be included in or communicating with the body activity monitor. The discriminator functions to determine the position and/or activity of the subject by determining the proximity of the subject to various devices and locations, such as exercise equipment and buildings. For example, it may be determined that the subject is close to running shoes to discriminate the activity of running. In a more advanced configuration, proximity to running shoes may be combined with GPS signals, heart rate sensor and/or motion sensor output to allow the activity calculator to determine the type of activity being performed, the duration of the activity, and the intensity of the activity.

When the user uses the system for the first time, he or she may designate certain movement patterns as correlating with certain activities. This will aid to calibrate the activity monitor.

Each of the described activity monitors and sensors is designed to be placed on a single position on the body. Bodily signals such as acceleration and ECG signals, are measured local to the position where the sensor is attached to the object. For example, acceleration measured by an accelerometer on the wrist includes motion of the arm, which is not detected by an accelerometer mounted on the waist.

The existing activity monitors, including for example a wrist strap or a waist belt, are often designed to be worn on one place on the body. The existing activity monitor is calibrated such that it provides accurate results if it is attached at a predefined location on the body. If the activity monitor is attached at a different location, the measured activity may be less accurate. If the activity monitor is not attached at the reference position, errors exceeding 5% in the estimation of energy expenditure may occur. This amounts to an error exceeding approximately 100 kilocalories per day.

SUMMARY OF THE INVENTION

It is an object of the invention to provide a measuring system that yields a more accurate estimate of a parameter relating to a subject.

According to the invention, this object is achieved in that
the sensor is arranged to be attached at one of a plurality of positions on the subject,
the measuring system further comprises means for establishing the position of the sensor on the subject, and
the means for deriving the subject-related value is arranged for deriving the subject-related value also in dependence on the position of the sensor on the subject.

With these provisions, the accuracy of the derived value is guaranteed for any of a plurality of positions on the body. The subject may attach the sensor at any preferred position on the body, and can preferably attach it at a different position whenever he or she desires to do so.

Subjects may have different preferences where they prefer wearing the sensor, and the same subject may prefer wearing the sensor at different locations, depending on for example the location of the subject, the local weather, or the activity the subject is performing at any given time. Advantageously, a plurality of sensors are attached at different positions on the subject and the means for deriving the subject-related value is arranged for combining the respective obtained measured values in order to increase the accuracy of the derived value.

The invention is particularly suitable for determining a derived value relating to a human or an animal.

According to an aspect of the invention, the plurality of positions includes at least two of the following: a wrist, a lower arm, an upper arm, a lower leg, an upper leg, a waist, a chest, a neck, a head. This allows for an especially flexible use of the activity monitor, because the positions mentioned are especially well suited for measuring the activity of the subject, and they are particularly convenient for wearing a sensor device.

According to another aspect of the invention, the derived value comprises an activity parameter of the subject. With this aspect, the measuring system becomes an activity monitor that enables to monitor the degree of activity performed by the subject. Other possible derived values include a temperature value or an ECG value that is automatically compensated for by the location of the sensor. Advantageously, the position of the sensor on the subject is established in dependence on an accelerometer measurement and a temperature or ECG value is compensated for in dependence on the established position.

According to an aspect of the invention, the activity parameter comprises energy expenditure. This makes the activity monitor particularly suitable for use in weight management.

According to another aspect of the invention, the activity parameter represents the degree of activity of the body part the sensor is attached to. When the position of the sensor on the subject is known, it becomes possible to monitor activity parameters related to a specific body part. For example, if the sensor is attached to the arm, the activity monitor can track energy expenditure, and in addition can track local acceleration of the arm. For example, with additional information provided by fitness equipment, the forces applied to the arm can be estimated and combined with acceleration information provided by the sensor to obtain local energy expenditure. This enables subjects to optimize a training schedule to train a specific body part. Also, if a predefined safety limit is exceeded, this can be provided as feedback to the user to avoid potentially dangerous situations.

According to an aspect of the invention, the measured value comprises at least one of temperature, ECG, or acceleration, in particular tri-axial acceleration. These examples of measured values are correlated with activity.

According to another aspect of the invention, the system further comprises means for selecting a subset of a predefined set of further physical and/or physiological quantities of the subject in dependence on the position of the sensor on the subject, and the sensor is arranged for generating a further measured value for each quantity in the selected subset. The subset may contain zero or more further physical and/or physiological quantities of the subject, for example temperature, ECG, or acceleration. This aspect allows the system to generate measurements that are particularly relevant to the body part the sensor is attached to. For example, a temperature measurement may provide relevant information when the temperature sensor is attached to the trunk of the body, and not when it is attached to, for example, an ankle. The system can take this into account for example by disregarding, or compensating, temperature measurement if the sensor is attached to an ankle. Further physical and/or physiological quantities, such as heart rate or temperature, can be used alongside for example a derived activity parameter in various health applications.

According to another aspect of the invention, the system further comprises
means for converting the measured value into an estimated measured value related to a reference position on the subject, and
means for deriving the subject-related value from the estimated measured value.

This aspect allows the measuring system to accurately measure, for example, an activity parameter with the sensor at one of a plurality of positions on the subject, even if the measuring system is calibrated for only a single reference position, because the deviation of the measured value caused by wearing the activity monitor at a different position is compensated for. The accuracy may be increased even further by calibrating a plurality of reference positions. In case a plurality of reference positions is calibrated, and the sensor is attached at a position that is not a reference position, the means for converting can compensate the measured value with respect to the nearest reference position or with respect to a weighted average of reference positions, thereby increasing the accuracy further.

Another aspect of the invention is characterized in that the means for determining the position of the sensor on the subject is arranged for determining the position in dependence on the measured value. This allows the sensor to be attached at different positions on the subject, without any additional user interaction to indicate the actual position of the device.

According to another aspect of the invention, it further comprises means for obtaining from the sensor a plurality of measured values measured during a time interval, and wherein the means for determining the position of the sensor on the subject is arranged for determining the position in dependence on the measured values measured during the time interval. This allows the position of the sensor to be determined in an especially reliable manner.

According to another aspect of the invention, the means for determining the position of the sensor on the subject is arranged for determining the position on the basis of a predefined set of rules related to the measured value or measured values measured during the time interval, respectively. A set of rules, preferably part of a rule-based system, possibly making use of fuzzy logic, is particularly suited for determining the position of the sensor.

According to another aspect of the invention, the means for determining the position of the sensor on the subject comprises means for performing a pattern recognition of a signal derived from the measured values measured during the time interval. A pattern recognition means is especially favorable to achieve a high reliability in establishing the position of the sensor on the subject.

According to an aspect of the invention, it further comprises means for determining that the user is performing a standardized activity, and the means for determining the position of the sensor on the subject is arranged for using at least one measured value obtained from the sensor, the measured value relating to a time the user is performing the standardized activity. This allows the activity monitor to determine the position of the device on the body with greater certainty. Preferably, the standardized activity has a repetition pattern with a cycle time of, for example, 1 to 2 seconds and the standardized activity is performed for at least five cycles.

According to another aspect of the invention, the means for establishing that the user is performing a standardized activity is arranged for establishing the activity in dependence on at least one measured value. This increases the accuracy and reduces the amount of required user interaction.

Another aspect of the invention further comprises a user interface for receiving input from a user for indicating when the subject is performing the standardized activity. This allows a very economical implementation of the activity monitor.

Another aspect of the invention further comprises a user interface for receiving input from a user related to the position of the sensor on the subject. This allows a very economical implementation of the activity monitor.

Another aspect of the invention further comprises
means for establishing that the subject is performing a predetermined activity,
storage means for storing at least one pattern related to performing the predetermined activity in a predetermined manner,
means for determining a similarity measure relating to a signal representing the derived value and the stored pattern, and
means for providing feedback in dependence on the similarity measure.

If the sensor position and the type of activity are known, the actual body movements can be compared to movements that are "optimal" for that particular activity. This translates into a measure of efficiency and proficiency in the selected activity. For example, inexperienced runners have a larger vertical acceleration component than experienced runners. Optimal movement patterns can be looked up in a database with key (desired activity, body part), and a pattern-matching technique can be used to determine how the actual pattern compares to the optimal pattern. Moreover, suggestions to change movement patterns of the specific body part can be given, such as for example, "when striking a ball with a racket, try to move in a continuous circular motion, and do not stop the motion after impact, to maximize acceleration of the ball upon impact". Alternatively, movements associated with health problems such as a baseball-arm, can be detected and feedback can be provided about the undesired movements.

According to another aspect of the invention, the means for establishing that the subject is performing the predetermined activity is arranged for establishing that the subject is performing at least one of a predetermined number of predetermined activities. This allows the activity monitor to distinguish between a plurality of activities of the subject, so that feedback can be provided in relation to the established activity.

According to another aspect of the invention, it further comprises a further sensor arranged to be attached to the subject for obtaining a further measured value representing a further physical or physiological quantity of the subject, and wherein the means for deriving the subject-related value is arranged for deriving the measured value also in dependence on the further measured value. Advantageously, a plurality of sensors are attached at different positions on the subject and the means for deriving the subject-related value is arranged for combining the respective obtained measured values in order to increase the accuracy of the derived value. Advantageously, the sensors communicate with each other or with a central unit, for example by means of a wireless or wired connection, for coordinated processing of the obtained measured values.

The system for determining the calorie balance of a subject according to the invention is characterized in that it comprises the activity monitor set forth, means for monitoring food consumption, and means for deriving the calorie balance using the derived energy expenditure. This system can provide accurate calorie balance because the activity parameter is determined with a high degree of accuracy.

The method according to the invention is characterized in that
the method further comprises the step of determining the position of the sensor on the subject, and
the step of deriving the subject-related value is performed also in dependence on the position of the sensor on the subject.

BRIEF DESCRIPTION OF THE DRAWINGS

These and other aspects of the method of the invention will be further elucidated and described with reference to the drawing, in which.

DETAILED DESCRIPTION OF THE INVENTION

Figure 1A:
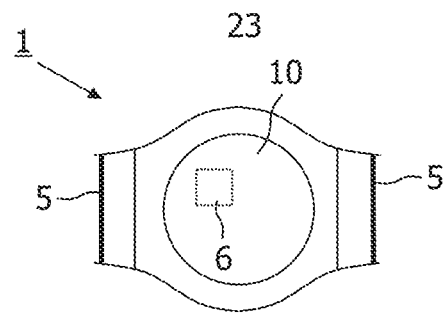
FIGS. 1A, 1B, 1C, and 1D show sketches of a device with attachment means that can be attached at several positions on a subject.
Figure 1B:
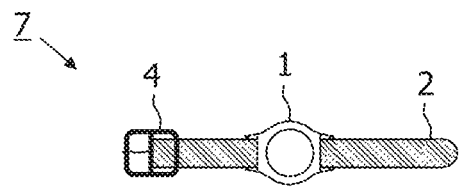
Figure 1C:
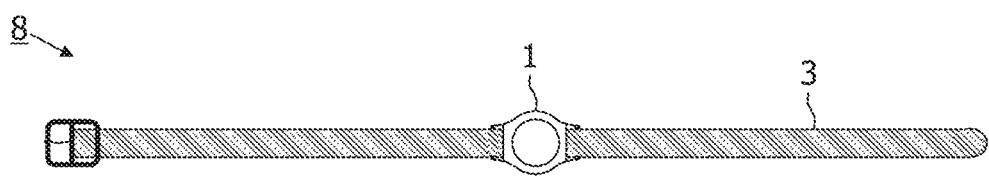
Figure 1D:
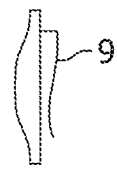

FIG. 1A shows an activity monitor 1 comprising a sensor 6 (shown in dotted lines), a display 10, and strap attachment means 5. The activity monitor 1 further comprises a microprocessor (not shown) for computing and displaying an activity parameter. The sensor 6 can comprise a single-axial or multi-axial accelerometer, a temperature sensor, an electrical sensor for measuring electrical body signals such as the ECG signal, a heart rate sensor, a pedometer, a global or local positioning system, or any other type of sensor. Such sensors are known to the skilled artisan. FIG. 1B shows the activity monitor 1, fixed to a short strap 2 with a buckle 4, and FIG. 1C shows the activity monitor 1 fixed to a long strap 3. The short strap 2 is suitable for attaching the activity monitor to a wrist or ankle, while the long strap 3 is suitable for attaching the activity monitor to a waist or chest. FIG. 1D shows a side view of the activity monitor illustrating a clip 9 fixed to the back of the activity monitor, making it possible to attach the activity monitor to clothing. The activity monitor with accessories as shown can be attached at one of a plurality of positions on a subject. The display 10 can be a touch-screen display for having a subject provide input to the activity monitor.

Figure 2:
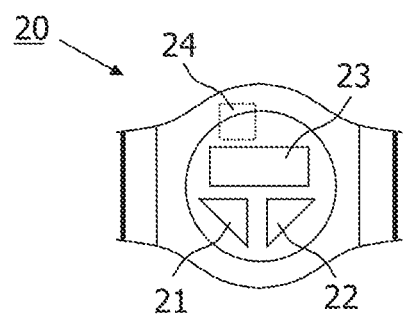
FIG. 2 shows an activity monitor with user interface.

FIG. 2 shows an activity monitor 20 with at least one button 21, 22, a display 23, and a sensor 24. The button can be used for receiving input from a user. Preferably, more buttons are provided to make it easier for the subject to provide different kinds of input to the activity monitor.

Figure 3:
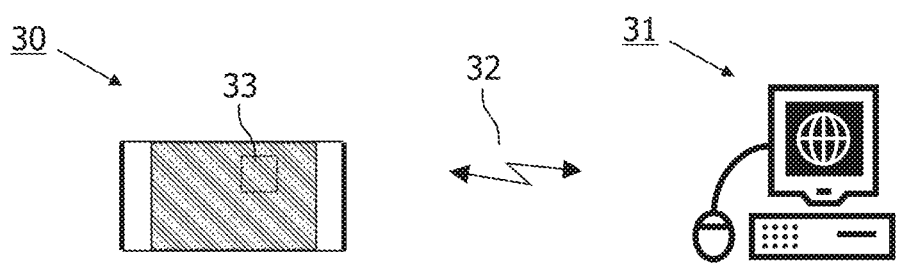
FIG. 3 shows an activity monitor comprising a device with a sensor connected to a separate unit by means of a wireless link.

FIG. 3 shows an activity monitor comprising a device 30 with a sensor 33. The device 30 does not have any buttons or display. The device 30 has means to communicate with a separate unit 31, preferably using a wireless link 32 such as WIFI or BLUETOOTH. The separate unit 31 is used to control the device 30. The separate unit 31, for example a personal computer or a personal digital assistant, comprises a microprocessor (not shown) for processing the information gathered by the device 30 by means of sensor 33. The separate unit 31 further comprises means for receiving user input and communicating the processed information to a user.

Figure 4:
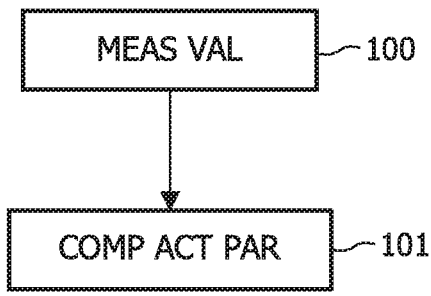
FIG. 4 shows a diagram of an embodiment of the method according to the invention.

FIG. 4 shows an embodiment of the method according to the invention for activity monitoring applicable to the case where the sensor 6 is attached at a reference position. In step 100, the sensor 6 delivers a measurement value at the reference position. Preferably, the sensor 6 is a tri-axial accelerometer, and the measurement value is a triple containing acceleration information in X, Y, and Z-directions. In step 101, the activity monitor computes the corresponding activity parameter, for example energy expenditure. For a tri-axial accelerometer attached to the back of the waist, a method to compute the corresponding energy expenditure is disclosed in "Daily physical activity, energy expenditure and physical fitness; assessment and implications" by Guy Plasqui, Ph.D. thesis, Maastricht University, 2004, referred to hereinafter as "Plasqui". The back of the waist is near the center of the body and a tri-axial accelerometer attached thereto provides a good estimation of overall movements.

Figure 5A:
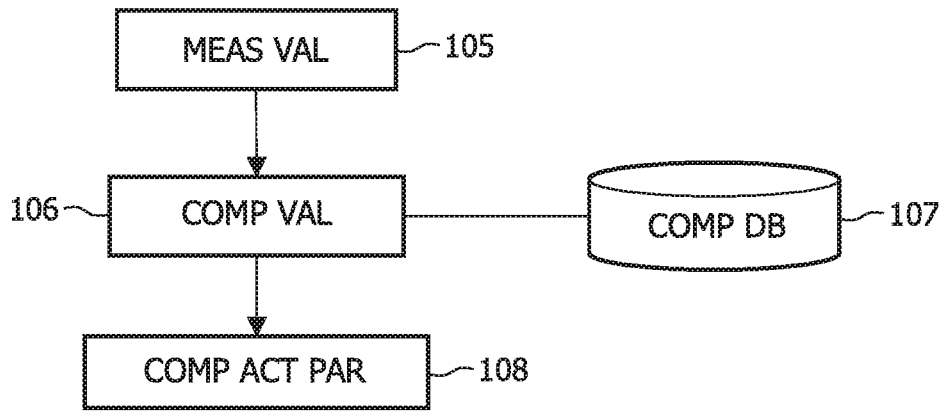
FIGS. 5A and 5B show diagrams of embodiments of the measuring method according to the invention including the compensation method according to the invention.

FIG. 5A shows an example of embodiment of the method according to the invention for activity monitoring applicable to the case where the sensor 6 is attached at a position on the subject that is not a reference position. In step 105, the sensor 6 delivers a measurement value measured at the position where the sensor is attached. After this, in step 106, the measurement value is compensated for the difference of the value at the position the sensor 6 is attached and the corresponding value at the reference position. After this, in step 108, the activity parameter, in this case energy expenditure, is computed using the method of computing the corresponding energy expenditure disclosed in Plasqui. The compensation method of step 106, in a very simple version, in this embodiment can be expressed as:

$$x_{corrected} = a + b x_{raw},$$

where $x_{raw}$ represents the measured value at the position where the sensor 6 is attached, $x_{corrected}$ is the corrected measured value, and a and b are compensation constants that have been stored in a compensation database 107 as part of an initialization procedure. In a multivariate system, where the measurement value comprises a tuple, for example the X, Y, and Z-components measured by a tri-axial accelerometer, the compensation method can be expressed as:

$$x_{corrected,i} = a_i + b_{i,1} x_{raw,1} + b_{i,2} x_{raw,2} + \ldots + b_{i,N} x_{raw,N},$$

where $x_{raw,1}, x_{raw,2}, \ldots, x_{raw,N}$ represent the N components of the measurement value tuple; $x_{corrected,i}$ represents the i-th component of the corrected measurement value tuple $(x_{corrected,1}, x_{corrected,2}, \ldots x_{corrected,N})$, and $a_i$ and $b_{i,j}$, for i, j=1, 2, . . . , N, are compensation constants that have been stored in a compensation database 107 as part of an initialization procedure. This example of a compensation method is particularly easy to implement. Other, potentially more flexible compensation methods are easily conceivable. Such methods include higher order polynomials, generalized linear models, other statistical methods, artificial neural networks, and fuzzy logic methods.

Figure 5B:
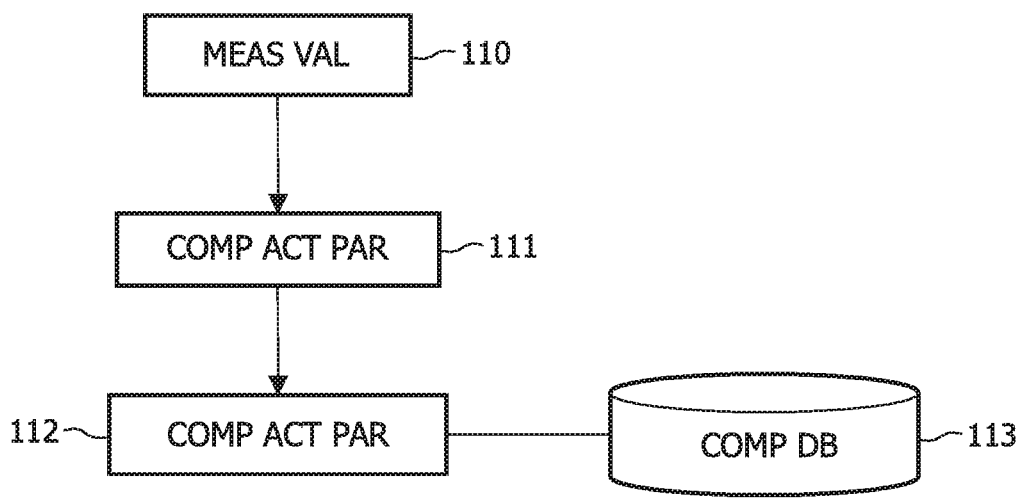

FIG. 5B shows an alternative embodiment of the method according to the invention for activity monitoring applicable to the case where the sensor 6 is attached at a position on the subject that is not a reference position. In step 110, the sensor 6 delivers a measurement value measured at the position where it is attached. After this, in step 111, the activity parameter, in this case energy expenditure, is computed using the method of computing the corresponding energy expenditure disclosed in Plasqui. Finally, in step 112 the computed energy expenditure is compensated for the difference of the energy expenditure as computed from the value measured at the position where the sensor 6 is attached and the "real" energy expenditure that would have been obtained if the sensor had been attached at the reference position. The compensation method, which is similar to the compensation method appearing in the embodiment according to FIG. 5A, makes use of the information stored in the compensation database 113.

Figure 6:
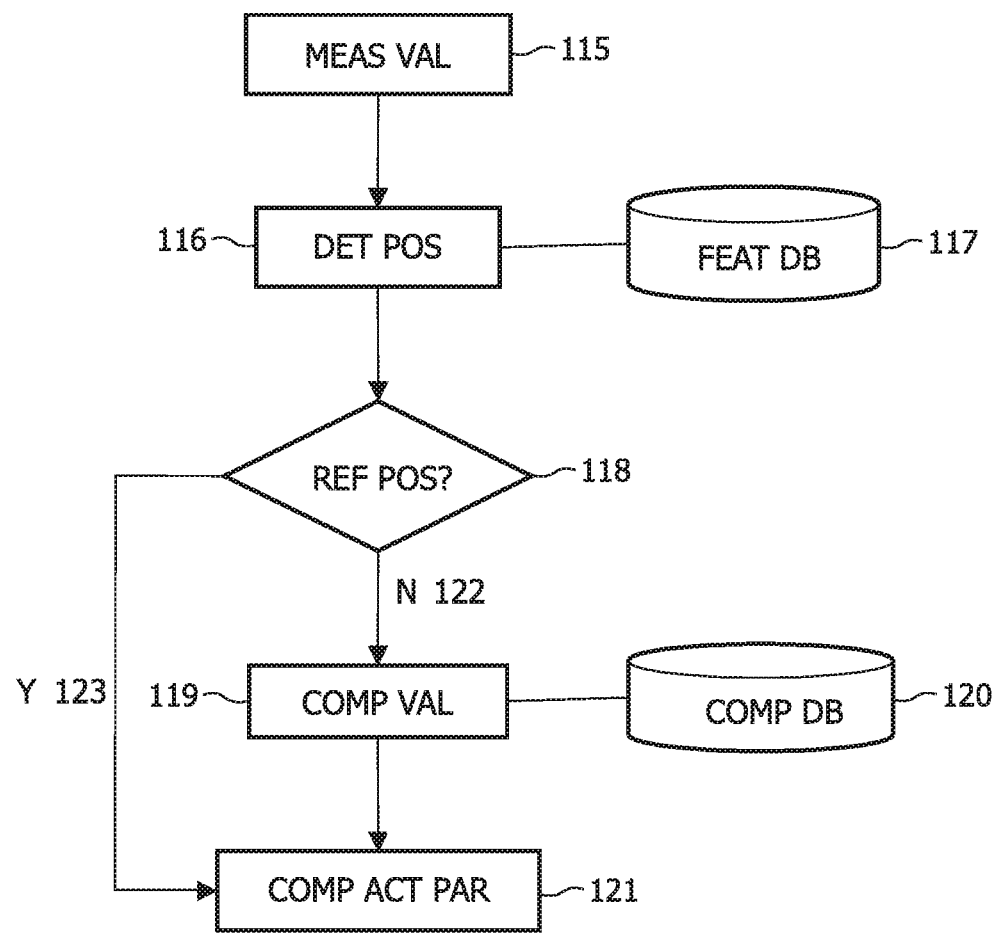
FIG. 6 shows a diagram of an embodiment of the method according to the invention including the method according to the invention to determine the position of the sensor on the subject.

FIG. 6 shows a diagram of an embodiment of a method of determining the position on the subject where the sensor 6 is attached and of computing the activity parameter, regardless of where the sensor was attached. In step 115, the measured value or a sequence of measured values is obtained from the sensor 6. Next, the position on the body is determined in step 116, using information from a feature database 117. To determine the position of the sensor 6 on the body, the signal from the sensor is analyzed for features that are position-dependent. Also, the subject is instructed to perform predefined standardized activities, such as walking, sitting, and standing, preferably for about 20 seconds each. Alternatively, the user can provide the activity monitor with input to indicate when he or she performs a standardized activity, and possibly, which standardized activity he or she performs. Combinations of the values during the standardized activities or the absolute measured values are used to determine the position of the sensor 6 on the subject. Thereto, a number of predefined rules are used. These rules can be in the form of "if . . . then" rules. An example of such a rule is: "if the measured value during walking is in the range of A to B times higher than during sitting, the sensor 6 is positioned on the lower arm", where A and B are constants stored in the feature database 117. Another example of such a rule is: "if the measured value during walking is in the range of C to D, the sensor 6 is positioned on the leg", where C and D are constants stored in the feature database 117. The rules can also be implemented in terms of fuzzy logic rules. Other ways to provide a set of rules, including for example neural network methods and logic programming, are obvious to the skilled artisan. In a preferred embodiment, the position of the sensor 6 on the subject is determined by means of pattern recognition. The pattern recognition can be performed for example by correlating a signal obtained from the sensor with a signal stored in the feature database 117. The pattern recognition can be performed in the time domain, the frequency domain, or another domain, preferably a time-frequency domain such as a wavelet domain. Pattern recognition can be performed in many ways known to the skilled artisan. For example, techniques used in speech recognition can be applied.

After the position of the sensor 6 on the subject has been determined in step 116, and the position is not a reference position (step 118, branch 122), in step 119 the measured value is compensated for by the difference between the value at the position at which the sensor is attached and the corresponding value at a reference position, making use of the information in a compensation database 120, in a way similar to the embodiment according to FIG. 5A. However, if the position is a reference position (step 118, branch 123), the method continues to step 121 Finally, in step 121 the activity parameter is computed from the possibly compensated measured value in a way similar to the embodiment according to FIG. 5.

In another embodiment, the measured value is first converted to an activity parameter, and the activity parameter is used to determine the position of the sensor 6 on the subject in a way similar to what is described above. In that case, after the position has been determined, the computed activity parameter is compensated for the difference between the computed activity parameter and the corresponding activity parameter computed from a value measured at a reference position, while information stored in a compensation database is made use of in a way similar to the embodiment according to FIG. 5B. It is also possible to use other quantities relating to measured values obtained from the sensor 6, in the step to determine the position 116 and/or in the step to compensate for the difference 119.

Figure 7:
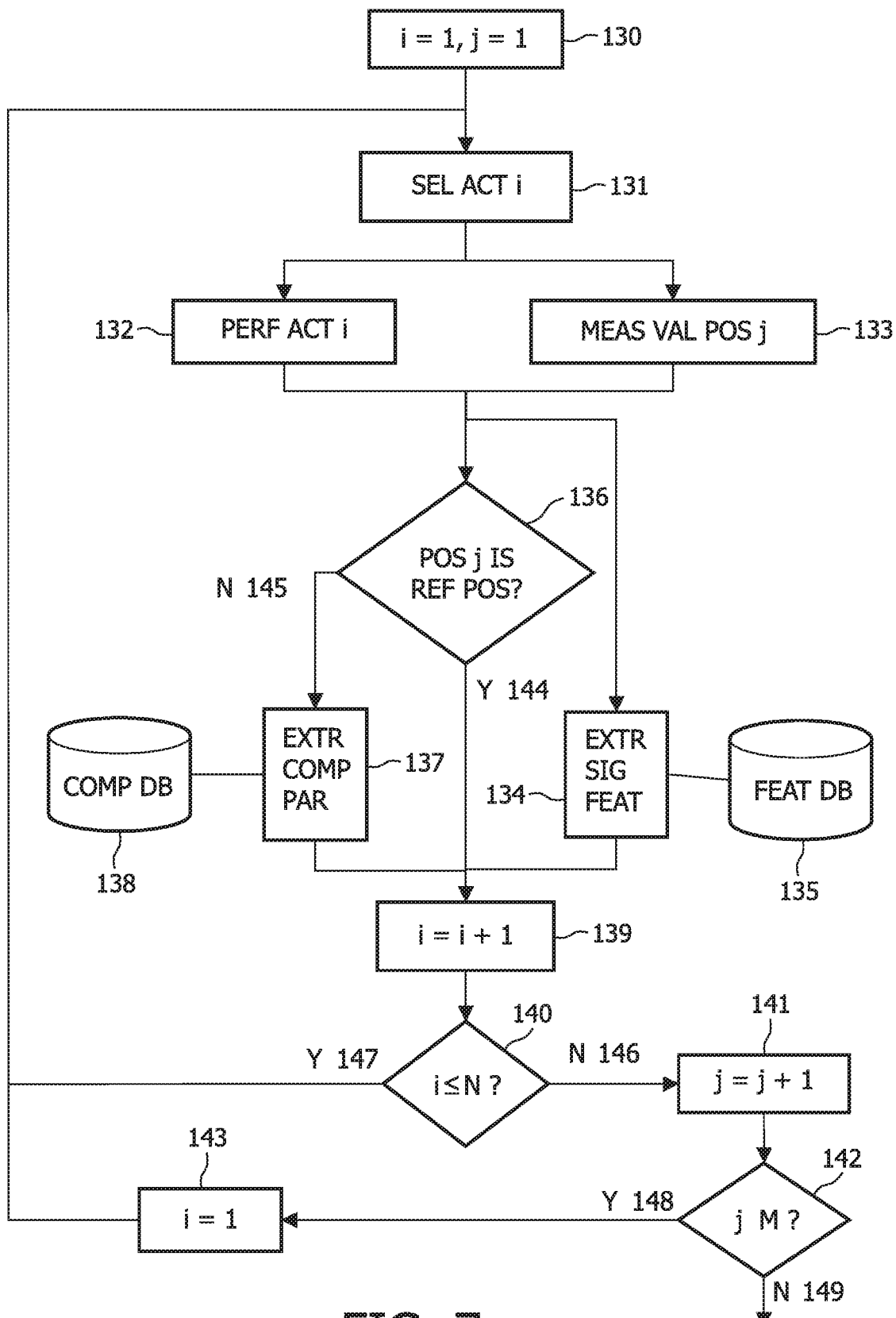
FIG. 7 shows a diagram of an embodiment of the method according to the invention including the compensation initialization method according to the invention.

FIG. 7 shows a diagram of an embodiment of an initialization procedure for the compensation database. In this embodiment, a sequence of steps is performed iteratively. As a first step 130, i and j are both initialized to 1. Each iteration starts with step 131 comprising an instruction to the subject to perform predefined activity i. The instruction can comprise a spoken instruction to walk, sit, or stand, or it can for example comprise showing the activity on a display for a predefined duration. Then, in step 132 the subject performs the predefined activity i, while the sensor 6 attached at position j on the subject measures a physical value, in this case tri-axial acceleration, in step 133. Next, in step 134 the essential features are extracted from the measured value signal and stored in a feature database 135. These essential features may comprise decision rules or constants that are part of decision rules, similar to the constants A, B, C, and D appearing in the description of the embodiment according to FIG. 6. Similarly, essential signal patterns can be stored in the time domain, frequency domain, time-frequency domain, or any other domain or combination of domains. Simultaneously, if position j is not a reference position (step 136, branch 145), in step 137 compensation parameters describing the difference between the measured value at the position of the sensor 6 on the subject and the corresponding value at a reference position are determined and stored in a compensation database 138. However, if position j is a reference position (step 136, branch 144), then the method proceeds to step 139. These compensation parameters may comprise constants appearing in the compensation method, similar to the constants a, b, $a_i$, and $b_{i,j}$ occurring in the description of the embodiment according to FIG. 5A.

To conclude an iteration, i is increased in step 139, and if i is smaller than or equal to the number of predefined activities (step 140, branch 147), the iteration steps are repeated; otherwise (step 140, branch 146), j is increased in step 141, and if j is smaller than or equal to the predefined number of positions (step 142, branch 148), i is set to 1 in step 143 and the iteration steps are repeated. If j is greater than the predefined number of positions (step 142, branch 149), the initialization procedure is finished.

In general, this sequence could be paralleled further, for example by using a plurality of sensors 6 to measure the values at a plurality of positions on the subject simultaneously. In this embodiment, the steps of extracting compensation parameters and extracting essential signal features are performed in parallel. However, they can also be performed sequentially. In an alternative embodiment, the activity parameter is computed after the sensor 6 has delivered the signal in step 133, and before extracting essential features in step 134 and determining compensation parameters in step 137. It is also possible to compute at least one derived quantity from the values measured by the sensor 6, and perform the steps of extracting essential features and determining compensation parameters based on the derived quantity.

In another embodiment, the initialization of the compensation database and the feature database are performed on the basis of a population of subjects. All subjects are asked to perform the standardized activities, the measured values are obtained from the sensor 6 at multiple positions on the subject, and after the data of all subjects have been collected and stored in an intermediate database, the compensation database and the feature database are filled with values that are representative of the population. This embodiment has the advantage that the activity monitor needs to be initialized only once, possibly by the manufacturer, and after that an unlimited number of activity monitors can be produced using the same database values.

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. The carrier may be any entity or device capable of carrying the program. For example, the carrier may include a storage medium, such as a ROM, for example a CD ROM or a semiconductor ROM, or a magnetic recording medium, for example a floppy disc or hard disk. Further, the carrier may be a transmissible carrier such as an electrical or optical signal, which may be conveyed via electrical or optical cable or by radio or other means. When the program is embodied in such a signal, the carrier may be constituted by such cable or other device or means. Alternatively, the carrier may be an integrated circuit in which the program is embedded, the integrated circuit being adapted for performing, or for use in the performance of, the relevant method. A measuring system comprises a sensor arranged to be attached to a subject for obtaining a measured value representing a physical or a physiological quantity of the subject. The measuring system further comprises means for deriving a subject-related value from the measured value. The sensor is arranged to be attached at one of a plurality of positions on the subject. The measuring system further comprises means for establishing the position of the sensor on the subject. The means for deriving the subject-related value is arranged for deriving the subject-related value also in dependence on the position of the sensor on the subject.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A device for monitoring activity of a subject, the device comprising:
   a sensor attachable to a plurality of positions on a body of the subject, the sensor comprising an accelerometer configured to provide a measurement value descriptive of a motion of the subject;
   a processor in communication with the sensor; and
   a non-transitory storage medium storing instructions that, when executed by the processor, cause the processor to:
      determine a current position of the plurality of positions on the body of the subject at which the sensor is positioned;
      determine whether the current position is a predetermined reference position;
      when the current position is determined to be the predetermined reference position, compute an activity parameter of the subject from the measurement value; and
      when the current position is determined not to be the predetermined reference position, compensate the measurement value for a difference of the measurement value at the current position and a corresponding value at the predetermined reference position, and compute the activity parameter from the compensated measurement value.

2. The device of claim 1, wherein the processor determines the current position of the plurality of positions on the body of the subject at which the sensor is positioned by analyzing at least one predefined rule using the measurement value, and identifying the current position based on the analysis of the at least one predefined rule.

3. The device of claim 2, wherein the at least one predefined rule is an output of a machine-learning algorithm.

4. The device of claim 3, wherein the at least one predefined rule includes a neural network.

5. The device of claim 2, wherein the analysis of the at least one predefined rule comprises performing pattern recognition against the measured value in at least one of a frequency domain, a time domain, and a time-frequency domain.

6. The device of claim 1, wherein the sensor further comprises an electrical sensor for measuring an ECG signal of the subject to provide a further measured value from the current position.

7. The device of claim 1, wherein the sensor further comprises a heart rate sensor for measuring a heart rate of the subject to provide a further measured value from the current position.

8. The device of claim 1, wherein the sensor further comprises a global positioning system for determining a location of the subject.

9. The device of claim 1, wherein the sensor further comprises a temperature sensor for measuring a temperature of the subject to provide a further measured value from the current position.

10. The device of claim 1, wherein the activity parameter comprises at least one of energy expenditure or calorie balance.

11. The device of claim 1, wherein the activity parameter comprises a degree of activity of a body part to which the sensor is attached at the current position.

12. A non-transitory machine-readable medium storing instructions for execution by a processor, the non-transitory machine-readable medium comprising:
   instructions for receiving a measurement value from a sensor attached to a body of a subject, wherein sensor comprises an accelerometer and the measurement value is descriptive of a motion of the subject;
   instructions for determining a current position of the sensor from a plurality of positions on the body of the subject based on the measurement value;
   instructions for determining whether the current position is a predetermined reference position;
   instructions for computing an activity parameter of the subject from the measurement value when the current position is determined to be the predetermined reference position; and
   instructions for compensating the measurement value for a difference of the measurement value at the current position and a corresponding value at the predetermined reference position, and computing the activity parameter from the compensated measurement value, when the current position is determined not to be the predetermined reference position.

13. The non-transitory machine-readable medium of claim 12, wherein the instructions for determining the current position of the sensor comprise analyzing at least one predefined rule using the measurement value, and identifying the current position based on the analysis of the at least one predefined rule.

14. The non-transitory machine-readable medium of claim 13, wherein the at least one predefined rule is an output of a machine-learning algorithm.

15. The non-transitory machine-readable medium of claim 14, wherein the at least one predefined rule includes a neural network.

16. The non-transitory machine-readable medium of claim 12, wherein the activity parameter comprises a degree of activity of a body part to which the sensor is attached at the current position.

17. A method for execution by a processor for adapting an activity monitor to a placement of a sensor of the activity monitor on a body of a subject, the method comprising:
   receiving a measurement value from the sensor attached to a body of a subject, wherein sensor comprises an accelerometer and the measurement value is descriptive of a motion of the subject;

determining a current position of the sensor from a plurality of positions on the body of the subject based on the measurement value;

determining whether the current position is a predetermined reference position;

when the current position is determined to be the predetermined reference position, computing an activity parameter of the subject from the measurement value; and when the current position is determined not to be the predetermined reference position, compensating the measurement value for a difference of the measurement value at the current position and a corresponding value at the predetermined reference position, and computing the activity parameter from the compensated measurement value.

18. The method of claim 17, wherein determining the current position of the sensor comprises analyzing at least one predefined rule using the measurement value, and identifying the current position based on the analysis of the at least one predefined rule.

19. The method of claim 18, wherein the at least one predefined rule is an output of a machine-learning algorithm.

20. The method of claim 17, wherein the activity parameter comprises a degree of activity of a body part to which the sensor is attached at the current position.

* * * * *